US007092532B2

(12) United States Patent
Luo et al.

(10) Patent No.: US 7,092,532 B2
(45) Date of Patent: Aug. 15, 2006

(54) ADAPTIVE FEEDBACK CANCELLER

(75) Inventors: Henry Luo, Waterloo (CA); Horst Arndt, Kitchener (CA); André Vonlanthen, Waterloo (CA)

(73) Assignee: Unitron Hearing Ltd., Kitchener (CA)

( * ) Notice: Subject to any disclaimer, the term of this patent is extended or adjusted under 35 U.S.C. 154(b) by 314 days.

(21) Appl. No.: 10/402,213

(22) Filed: Mar. 31, 2003

(65) Prior Publication Data

US 2004/0190731 A1 Sep. 30, 2004

(51) Int. Cl.
*H04B 15/00* (2006.01)
*H04R 25/00* (2006.01)
*A61F 11/00* (2006.01)
*H03G 3/00* (2006.01)

(52) U.S. Cl. .......................... 381/93; 381/83; 381/318; 381/71.11; 381/107

(58) Field of Classification Search ................ 381/312, 381/318, 83, 93, 71.11, 95–96, 104, 107
See application file for complete search history.

(56) References Cited

U.S. PATENT DOCUMENTS

| | | | | |
|---|---|---|---|---|
| 6,072,884 | A | 6/2000 | Kates | |
| 6,125,187 | A * | 9/2000 | Hanajima et al. | 381/83 |
| 6,240,192 | B1 * | 5/2001 | Brennan et al. | 381/314 |
| 6,377,119 | B1 | 4/2002 | Hays | |
| 6,404,895 | B1 | 6/2002 | Weidner | |
| 6,434,246 | B1 | 8/2002 | Kates et al. | |
| 6,434,247 | B1 | 8/2002 | Kates et al. | |
| 6,885,752 | B1 * | 4/2005 | Chabries et al. | 381/321 |

OTHER PUBLICATIONS

Edwards et al., Signal-processing algorithms for a new software-based, digital hearing device, The Hearing Journal, Sep. 1998, vol. 51, No. 9, pp. 44, 46, 47, 50, 52.

Hellgren, Johan, Analysis of Feedback Cancellation In Hearing Aids With Filtered-X LMS and the Direct Method of Closed Loop Identification, IEEE Transactions On Speech and Audio Processing, vol. 10, No. 2, Feb. 2002, pp. 119-131.

Kuk et al., Understanding Feedback and Digital Feedback Cancellation Strategies, The Hearing Review, Feb. 2002, pp. 36, 38-41, 48-49.

Powers et al., Benefits of DSP: A Review—A look at DSP benefits beyond conventional instruments, The Hearing Review, Oct. 2000, pp. 62, 64-67.

Smriga et al., Problem Solving Through "Smart" Digital Technology, The Hearing Review, Jan. 1999, pp. 58-60.

* cited by examiner

*Primary Examiner*—Laura A. Grier
(74) *Attorney, Agent, or Firm*—Bereskin & Parr

(57) ABSTRACT

A system and method for adaptively removing feedback in audio systems and, more particularly, hearing aid systems. The audio system comprises an analysis unit, for receiving an input signal and providing N bandpass input signals, and an adaptive feedback cancellation unit for removing a feedback condition in one or more of the N bandpass input signals. The adaptive feedback cancellation unit comprises N sub-units with at least one of the sub-units including: (i) a feedback detector for indicating the presence of the feedback condition in one of the bandpass input signals, (ii) an adaptive feedback canceller for providing an adaptive gain modification factor for adjusting gain when the feedback condition is detected within one of the bandpass input signals, and (iii) a multiplier coupled to the adaptive feedback canceller and the analysis unit for providing a bandpass output signal based on one of the bandpass input signals and the corresponding adaptive gain modification factor.

34 Claims, 4 Drawing Sheets

ADAPTIVE FEEDBACK CANCELLER

FIELD OF THE INVENTION

The invention relates to audio systems and a method for adaptively canceling feedback. More particularly, the invention relates to a hearing aid system and method for adaptively canceling feedback while not impairing the speech comprehension of the user of the hearing aid system.

BACKGROUND OF THE INVENTION

Feedback in hearing aid systems is a well-known problem that can occur when there is a feedback path from the output signal of the hearing aid system to the input signal of the hearing aid system. This usually occurs when a user of the hearing aid system is moving his/her jaws (i.e. while eating), wearing a hat, using a telephone, standing close to walls, etc. The feedback usually occurs in mid and high frequency regions which are important for allowing the hearing aid user to understand speech. Accordingly, feedback is not only annoying but impairs speech comprehension for the hearing aid user. Feedback can also be due to other causes such as magnetic, vibrational or electrical.

Many different feedback reduction approaches have been developed to cancel feedback when it occurs in the hearing aid system. Some of these approaches comprise estimating a feedback path transfer function and altering the feedback path transfer function at critical frequencies (i.e. feedback prone frequencies) to remove feedback. The feedback path transfer function can be estimated via auto-correlation of the input signal and/or cross-correlation of the input signal and the output signal. This approach may also be adaptive by incorporating a variation of the Least Mean Square algorithm for adaptive estimation of the feedback transfer function. Consequently, this approach requires rather high levels of computational power, and due to the limited computational power of available digital hearing aid systems, the effectiveness of this approach is restricted particularly in dealing with the multiple feedback paths that usually occur in daily life.

Another approach for reducing feedback in hearing aid systems is to use a notch filter. A single notch filter may effectively reduce feedback when the overall loop gain in a single narrow frequency band reaches values larger than unity and the phase of the feedback signal is 0° or a multiple of 360° (i.e. the Nyquist criterion). If the loop gain begins to exceed unity and the corresponding phase satisfies the Nyquist criterion in several frequency bands that lie far apart, then several notch filters may be used. However, the notch filters have to be tuned to the correct frequencies at which the feedback occurs which implies that the frequencies and frequency bands where feedback occurs must be detected. Detection of a single frequency feedback signal in noise may involve signal processing techniques such as correlation and parametric modeling methods, followed by peak picking, zero crossing counters, etc., as is well known to those skilled in the art. Accordingly, this method of feedback cancellation also requires high levels of computational power that can exceed the computational power available in hearing aid systems.

Another approach for reducing feedback in the hearing aid system is anti-phase feedback canceling. This involves adaptively detecting changes in the feedback path, and once feedback is detected, generating an anti-phase feedback signal to cancel the feedback. If the hearing aid system is linear, the feedback path changes slowly, and only a small number of feedback paths exist (such as one or two), anti-phase feedback canceling works well. However, the feedback path can change dramatically and very rapidly in real-life situations. Furthermore, most of the advanced digital hearing aid systems are not linear and incorporate some type of input or output referred compression. Accordingly, the gain of the hearing aid system changes constantly as the input or output signal levels change. The feedback signal level is therefore not constant, as it is for a linear hearing aid system. In addition, multiple feedback paths usually occur as well as temporary feedback path changes. All of these factors result in high computational demand which can limit the application of the anti-phase feedback canceling technique in hearing aid systems, particularly when dealing with multi-feedback path situations.

Another approach for reducing feedback in the hearing aid system, while addressing the limited computational power in the hearing aid system, is to use a non-adaptive feedback manager. The most basic feedback manager is a static feedback manager that permanently reduces the maximum loop gain to prevent the occurrence of feedback in the hearing aid system. Although this approach can be effective, reducing the maximum system gain limits the user's access to higher gain, which may be required on occasion depending on the individual's hearing loss. Since feedback often occurs in the higher frequency range, which is also the frequency range that contains the consonant sounds of speech, reducing the gain in this frequency range can have detrimental effects on speech discrimination. In addition, the static feedback manager cannot dynamically compensate for temporary feedback caused when a hand or a telephone is placed close to or on the hearing aid system, or if the user distorts the ear canal with jaw movements.

Another characteristic of these prior art feedback reduction methods is that they typically require a few hundred milliseconds (i.e. 200 ms) to detect the occurrence of feedback and then another few hundred milliseconds (i.e. 200 ms) to eliminate the feedback. Accordingly, the user of the hearing aid system will hear a short, but very loud, burst of feedback before the feedback is suppressed. This is detrimental since such a feedback signal can be uncomfortable and annoying for the hearing aid user.

SUMMARY OF THE INVENTION

The present invention is directed towards a hearing aid system that reliably and rapidly detects feedback or the onset of feedback and rapidly eliminates the feedback once it is detected while requiring minimal computational cost. Accordingly, a wearer of the hearing aid system is not subjected to any annoying or upsetting feedback signals during a telephone call, or during meals and other daily activities requiring jaw movements. The feedback detection and elimination is adaptive in time, frequency and amplitude. Further, the elimination of feedback is done while maintaining good sound quality of the output sound signal to the user of the hearing aid system.

In accordance with a first aspect, the invention provides an audio system for receiving a time domain input signal having an input frequency spectrum and for providing a time domain output signal. The invention can remove feedback from the system or prevent feedback from occurring in the system. The audio system comprises an analysis unit for receiving the time domain input signal and for providing N bandpass input signals, each of the bandpass input signals corresponding to a portion of the input frequency spectrum, and wherein N is a positive integer. The audio system also comprises an adaptive feedback cancellation unit coupled to the analysis unit for receiving the N bandpass input signals and providing N bandpass output signals. The adaptive feedback cancellation unit comprises N sub-units. At least one of the sub-units is adapted to cancel feedback. The at least one sub-unit includes: (i) a feedback detector coupled to the analysis unit for receiving one of the bandpass input signals and providing a feedback detection signal for indicating the presence of a feedback condition in one of the bandpass input signals, (ii) an adaptive feedback canceller coupled to the feedback detector for receiving the feedback detection signal and providing an adaptive gain modification factor for adjusting gain when the feedback detection signal indicates the presence of the feedback condition within the bandpass input signals, and, (iii) a multiplier coupled to the adaptive feedback canceller and the analysis unit for providing one of the bandpass output signals based on one of the bandpass input signals and the adaptive gain modification factor. The audio system further comprises a synthesis unit for receiving the N bandpass output signals and for providing the time domain output signal.

In accordance with a second aspect, the invention provides a method for removing a feedback condition in a audio system. The audio system receives a time domain input signal having an input frequency spectrum and provides a time domain output signal. The method comprises:

a) converting the time domain input signal into one or more bandpass input signals, each of the one or more bandpass input signals corresponding to a portion of the input frequency spectrum;

b) providing one or more bandpass output signals corresponding to the one or more bandpass input signals wherein for at least one of the one or more bandpass input signals, the method comprises:

(i) providing a feedback detection signal for indicating the presence of the feedback condition in the at least one of the one or more bandpass input signals;

(ii) providing an adaptive gain modification factor for adjusting gain when the feedback detection signal indicates the presence of the feedback condition within the at least one of the one or more bandpass input signals; and, (iii) providing one of the one or more bandpass output signals by multiplying the at least one of the one or more bandpass input signals and the adaptive gain modification factor; and, c) combining the one or more bandpass output signals for providing the time domain output signal.

In another aspect, the invention provides an audio system for receiving a time domain input signal having an input frequency spectrum and for providing a time domain output signal. The audio system is adapted to remove a feedback condition within the time domain input signal. The audio system comprises an analysis unit for receiving the time domain input signal and providing N bandpass input signals. Each of the bandpass input signals correspond to a portion of the input frequency spectrum, and wherein N is a positive integer. The system further comprises an adaptive feedback cancellation unit coupled to the analysis unit for receiving the N bandpass input signals and providing N bandpass output signals. The adaptive feedback cancellation unit comprises N sub-units, wherein at least one sub-unit comprises means for canceling feedback by detecting the presence of the feedback condition in at least one of the bandpass input signals and providing at least one adaptive gain modification factor for adjusting gain for the at least one of said bandpass input signals to remove the feedback condition and provide at least one of the bandpass output signals. The system also includes a synthesis unit for receiving the N bandpass output signals and for providing the time domain output signal.

In another aspect, the present invention provides a method for removing a feedback condition in an audio system. The audio system is adapted to receive a time domain input signal having an input frequency spectrum and provide a time domain output signal. The method comprises:

a) converting the time domain input signal into one or more bandpass input signals, each of the one or more bandpass input signals corresponding to a portion of the input frequency spectrum;

b) providing one or more bandpass output signals corresponding to the one or more bandpass input signals wherein for at least one of the one or more bandpass input signals, the method comprises detecting the presence of the feedback condition and modifying the at least one of the one or more bandpass input signals with an adaptive gain modification factor for providing at least one of the one or more bandpass output signals; and, c) combining the one or more bandpass output signals for providing the time domain output signal.

BRIEF DESCRIPTION OF THE DRAWINGS

For a better understanding of the present invention and to show more clearly how it may be carried into effect, reference will now be made, by way of example only, to the accompanying drawings which show preferred embodiments of the present invention and in which.

DETAILED DESCRIPTION OF THE INVENTION

Figure 1:
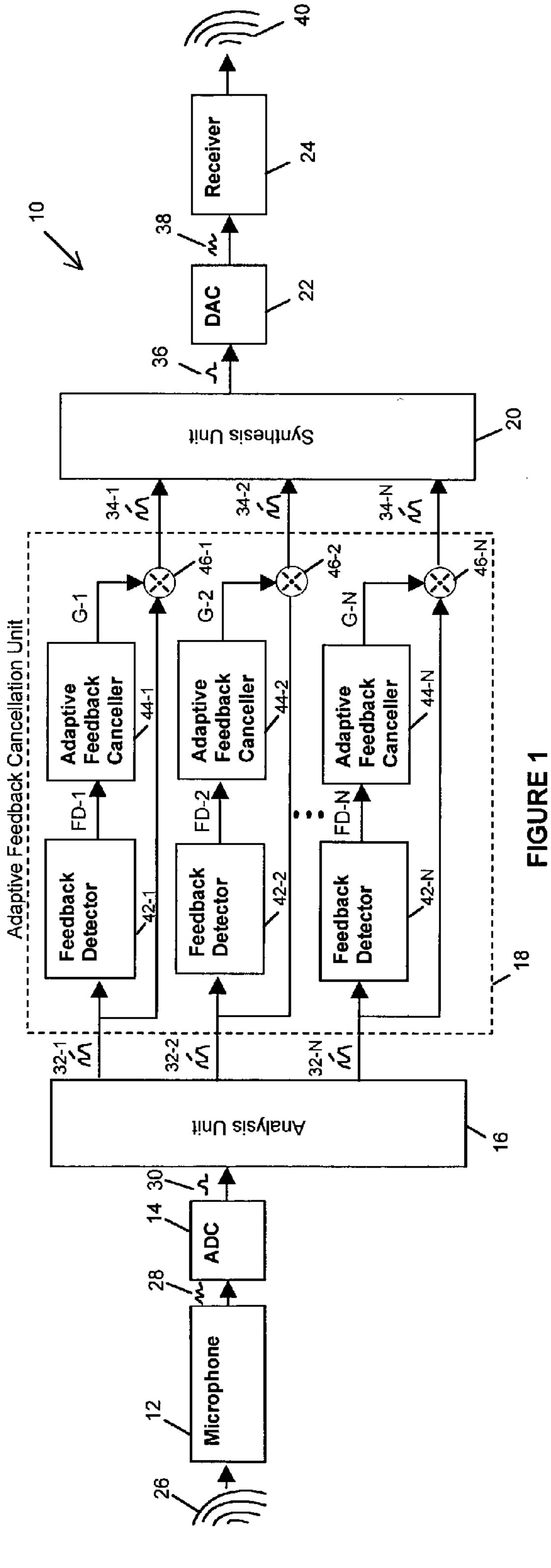
FIG. 1 is a block diagram of a first embodiment of a hearing aid system for adaptively detecting and canceling feedback in accordance with the present invention.

Reference is first made to FIG. 1, which illustrates a hearing aid system 10 that is a particular example of an audio system in accordance with a first preferred embodiment of the present invention. The hearing aid system 10 comprises a microphone 12, an analog-to-digital converter (ADC) 14, an analysis unit 16, an adaptive feedback cancellation unit 18, a synthesis unit 20, a digital-to-analog converter (DAC) 22 and a receiver 24. Alternate implementations can include other input means such as multiple microphones, an induction pick-up coil, a direct electrical input or a bone conduction input as is well known to those skilled in the art. For simplicity, this description focuses on a microphone input.

The microphone 12 receives an input sound signal 26 and provides an analog input signal 28 corresponding to input sound signal 26. The input sound signal 26 contains desirable audio information, noise and possibly feedback. The microphone 12 may be any type of sound transducer capable of receiving a sound signal and providing a corresponding analog electrical signal. The ADC 14 receives the analog input signal 28 and produces a time domain input signal 30 which is digital. The time domain input signal 30 has an input frequency spectrum. Further processing is preferably performed on the time domain input signal 30 such as framing and filtering with a low-pass filter. The time domain input signal 30 may then preferably be folded and added to generate a block of data for processing by the analysis unit 16. These operations are well known to those skilled in the art and are not shown in FIG. 1.

The analysis unit 16 receives the time domain input signal 30 and produces one or more bandpass input signals 32-1, 32-2, . . . , 32-N which each corresponds to a portion of the input frequency spectrum of the time domain input signal 30. The value of N may be any integer but is preferably a power of 2 such as 2, 4, 8, 16, etc. The analysis unit 16 may perform a time domain to frequency domain transform, such as the Fast Fourier Transform (FFT) or the Wavelet Transform, or may comprise a filter bank of FIR or IIR filters for providing the bandpass input signals 32-1, 32-2, . . . , 32-N. The analysis unit 16 preferably performs a 2N-point FFT to generate the bandpass input signals 32-1, 32-2, . . . , 32-N. In this case, the coefficients of the 2N-point FFT represent N frequency bands. The signal strength (i.e. input sound level) of the bandpass input signals 32-1, 32-2, . . . , 32-N can be determined from the corresponding FFT coefficient. The input sound level will vary with time and frequency.

Any one of the bandpass input signals 32-1, 32-2, . . . , 32-N may contain feedback. Accordingly, each of the bandpass input signals 32-1, 32-2, . . . , 32-N is processed by the adaptive feedback cancellation unit 18 which provides a corresponding set of bandpass output signals 34-1, 34-2, . . . , 34-N which do not have feedback. The synthesis unit 20 combines the bandpass output signals 34-1, 34-2, . . . , 34-N into a time domain output signal 36 which is a digital signal. Accordingly, the synthesis unit 20 may perform the Inverse Fast Fourier Transform (IFFT), the inverse Wavelet transform or may comprise a summer depending on the processing that is performed by the analysis unit 16. The time domain output signal 36 is then converted to an output analog signal 38 which is processed by the receiver 24 for providing an output sound signal 40 to the user of the hearing aid system 10. Alternatively, the receiver 24 may be a zero-bias receiver and the time domain output signal 36 may be directly applied to the receiver 24 without passing through the DAC 22.

The hearing aid system 10 further comprises other components for processing the bandpass input signals 32-1, 32-2, . . . , 32-N, as is commonly known to those skilled in the art, such as an amplification unit (not shown) and/or a noise reduction unit. The amplification unit applies a gain value to each of the bandpass input signals 32-1, 32-2, . . . , 32-N for amplifying these signals according to the hearing loss of the user of the hearing aid system 10 thereby allowing the user to hear speech. The amplification unit may utilize a linear gain curve, in accordance with typical linear hearing aid systems, as is commonly known to those skilled in the art, to calculate the gain values depending on the sound level of the bandpass input signals 32-1, 32-2, . . . , 32-N. Alternatively, the amplification -unit may utilize a non-linear gain curve, in accordance with typical compression hearing aid systems, as is commonly known to those skilled in the art, to calculate the gain values depending on the sound level of the bandpass input signals 32-1, 32-2, . . . , 32-N. This is discussed in further detail below.

The adaptive feedback cancellation unit 18 comprises a number of sub-units 18-1, 18-2, . . . , 18-N for processing each of the bandpass input signals 32-1, 32-2, . . . , 32-N. Each sub-unit of the adaptive feedback cancellation unit 18 comprises a feedback detector 42, an adaptive feedback canceller 44 and a multiplier 46. Using the first sub-unit 18-1 of the adaptive feedback cancellation unit 18 as an example for the remainder of this description, the bandpass input signal 32-1 is split into two parts; one part of the bandpass input signal 32-1 is received by the feedback detector 42-1 and the other part of the bandpass input signal 32-1 is received by the multiplier 46-1. The feedback detector 42-1 processes the bandpass input signal 32-1 to determine the presence of a feedback condition in the frequency range associated with the bandpass input signal 32-1. The feedback condition includes two scenarios: feedback already exists in the bandpass input signal 32-1 or there is the onset of feedback (i.e. the buildup of feedback) in the bandpass input signal 32-1. Accordingly, the feedback detector 42-1 provides a feedback detection signal FD-1 for indicating the presence of the feedback condition in the bandpass input signal 32-1. The feedback detection signal FD-1 may be a binary signal, for example, with a value of 1 for indicating the presence of the feedback condition and a value of 0 for indicating that the feedback condition is not present.

The adaptive feedback canceller 44-1 receives the feedback detection signal FD-1 and computes an adaptive gain modification factor G-1 with an appropriate magnitude when the feedback condition has been detected. The adaptive gain modification factor G-1 adjusts the amount of gain that is applied to the bandpass input signal 32-1 by the amplification unit for removing feedback or preventing the further buildup of feedback within the bandpass input signal 32-1. If the feedback condition is not detected within the bandpass input signal 32-1 then the adaptive feedback canceller 44-1 may provide an adaptive gain modification factor G-1 with a magnitude of 1. The multiplier 46-1 multiplies the bandpass input signal 32-1 with the adaptive gain modification factor G-1 to produce the bandpass output signal 34-1.

The feedback detectors 42-1, 42-2, . . . , 42-N continuously monitor the bandpass input signals 32-1, 32-2, . . . , 32-N to detect the feedback condition in real time independently and simultaneously in all N frequency bands. The feedback detectors 42-1, 42-2 . . . , 42-N also utilize a sliding time window to analyze the corresponding bandpass input signal 32-1, 32-2, . . . , 32-N. The size of the sliding time window and the rate at which the sliding time window is updated can be selected to allow for the rapid detection of the feedback condition in the bandpass input signals 32-1, 32-2, . . . , 32-N. The simultaneous and independent monitoring of a plurality of frequency bands allows for the detection of multiple, simultaneous feedback paths. Furthermore, most modern hearing aid systems employ FFT or filter-bank processing (i.e. the analysis unit 16) to modify the input sound signal according to the hearing loss of the hearing aid system user. Accordingly, the adaptive feedback cancellation scheme of the present invention does not add an excessive amount of computational complexity to a hearing aid system but rather efficiently utilizes resources that are already present in the hearing aid system.

Figure 2:
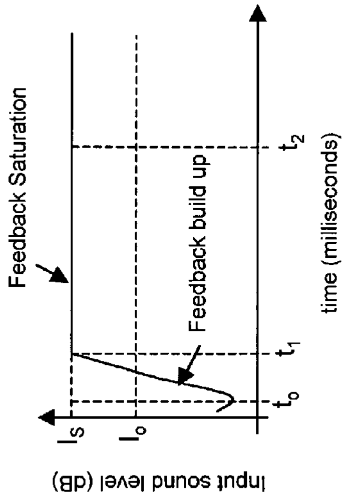
FIG. 2 illustrates a typical change in sound level that occurs during a feedback condition for a linear hearing aid system.

Feedback occurs when the closed-loop system gain of a hearing aid system is sufficiently high to cause the system to become unstable. Referring now to FIG. 2, shown therein is the development of feedback for a linear hearing aid system. The sound level of one of the bandpass input signals (i.e. input sound level) increases gradually due to feedback build-up from time $t_0$ to time $t_1$. During this time duration, an output sound signal is leaked from the receiver back to the microphone and is amplified by the hearing aid system to produce an output sound signal with a higher sound level. This process repeats itself as the sound level of the bandpass input signal crosses a sound level threshold $I_0$ after which saturation occurs at a sound level $I_s$ for the output and input sound signals. At the point of saturation, the output sound level is saturated and remains at a constant level over time and continues until the feedback loop is broken or feedback is removed from the bandpass input signal. As discussed previously, this feedback can occur for one or more frequencies.

Figure 3:
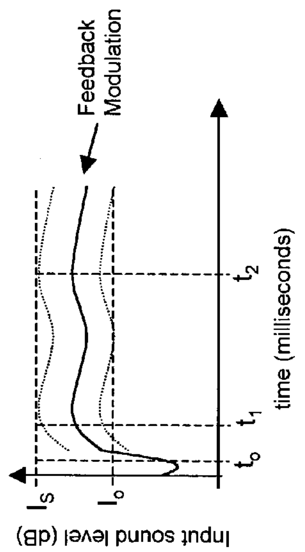
FIG. 3 illustrates a typical change in sound level that occurs during a feedback condition for a non-linear hearing aid system.

Referring now to FIG. 3, shown therein is the development of feedback for a non-linear (i.e. compressive) hearing aid system for a bandpass input signal. Once again, the input sound level increases gradually due to feedback build-up from time $t_0$ to time $t_1$ during which the input sound level crosses the sound level threshold $I_0$ and output limitation occurs for the sound levels of the output and input controlled compression system. In such non-linear hearing aid systems, the output sound level will not be saturated at a constant sound level $I_s$ but rather will be modulated between upper and lower bounds represented by the dotted lines in FIG. 3. The feedback will be modulated since, the compression unit of the non-linear hearing aid, will provide a gain reduction for an input sound signal with a high sound level. Accordingly, the sound level of the output sound signal will be reduced, which leads to a reduction in the sound level of the input sound signal that is leaked back to the microphone from the receiver. However, the compression unit will then apply a larger gain to the input sound signal that leads to a larger amount of feedback. This process repeats itself until the feedback loop is broken or feedback is removed from the input sound signal.

The degree of modulation in the feedback depends on the feedback path and the dynamic characteristics of the particular compression method that is used by the non-linear hearing aid system. These dynamic characteristics include attack and release times, the particular compression ratios that are used by the compression unit and the interactive relationship between these parameters. Typical level variations for a modulated feedback signal are system dependent and may range from 6 to 10 dB, while the feedback modulation frequency could vary from a few Hz to a few hundred Hz.

In practice, most natural sound signals such as speech or music are continuously changing in frequency and amplitude over time. The inventors have realized that monitoring the temporal variations of various parameters of the bandpass input sound signal, for different frequency regions, will provide information that can be used to detect the onset of feedback or that feedback is present. The temporal monitoring preferably detects the onset of feedback early in the feedback buildup phase so that the feedback can be removed before saturation occurs. A typical feedback buildup phase in a hearing aid system can be as long as a few hundred milliseconds in duration. Performing the temporal monitoring in different frequency regions (i.e. frequency bands) allows for efficiently processing multiple feedback paths at the same time. The inventors have found that this combination of temporal and frequency monitoring results in a reduction of the duration and level of feedback so that the feedback is barely noticeable to the user of the hearing aid system.

Figure 4:
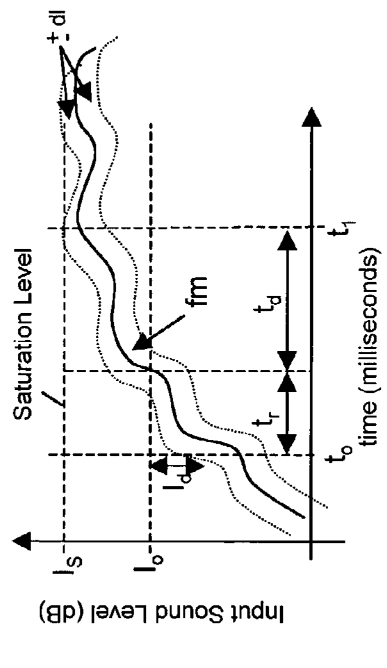
FIG. 4 is a magnified view of the change in sound level of FIG. 3.

Referring now to FIG. 4, shown therein are various detection parameters of the input sound level of the bandpass input signals 32-1, 32-2, . . . , 32-N that can be monitored by the feedback detectors 42-1,42-2, . . . , 42-N to quickly detect the onset of feedback for a particular frequency band. The input sound level is preferably represented by the magnitude of the corresponding FFT coefficient provided by the analysis unit 16. The detection parameters that may be used to detect the onset of feedback or the presence of feedback include input sound level, input sound level variation, input sound level modulation, rise time duration, and gain differential. These detection parameters will be described in relation to bandpass input signal 32-1 and feedback detector 42-1. It should also be understood that during the operation of the hearing aid system 10, average values for these detection parameters are measured on data blocks of the bandpass input signals. The data blocks have a pre-specified time duration and a sliding window is used in constructing the data blocks. The time duration of each data block can be adjusted to allow the hearing aid system to more quickly attack feedback (by reducing the time duration of each data block) or more slowly attack feedback (by increasing the time duration of each data block).

The inventors provide numerical examples for the parameters that are used to detect the onset or presence of feedback in a hearing aid system. These numerical examples are typical for one particular hearing aid system used by the inventors. It should be understood by those skilled in the art that the numerical values of the detection parameters are strongly influenced by the hearing aid system itself and the nature of the feedback paths encountered in a real-life hearing aid use situation and some can vary by a factor of, for example, 2 or 3 from the exemplary values of the detection parameters provided herein.

The input sound level parameter is the sound level of the bandpass input signal 32-1. The sound level distance $I_d$ of the input sound level from the feedback threshold level $I_0$ provides an indication of the possibility that feedback is occurring for the bandpass input signal 32-1. The sound level distance $I_d$ may be monitored to detect the onset of feedback within the bandpass input signal 32-1. The onset of feedback (i.e. feedback buildup) can be detected when the sound level distance $I_d$ becomes smaller than a pre-specified sound level distance threshold. Alternatively, the presence of feedback can be detected when the magnitude of the input sound level crosses over the feedback threshold level $I_0$. A typical threshold level $I_o$ can be 48 dB, and $I_d$ can be 3 dB. The value for the sound level distance $I_d$ can be much larger depending on the particular hearing aid system and the sensitivity desired for the detection of feedback buildup.

The input sound level variation parameter dI represents the amount of variability in the sound level of the bandpass input signal 32-1. This parameter is related to the feedback path, the compression ratio, and the attack and release times used by the compression unit of a non-linear hearing aid. The onset of feedback in the bandpass input signal 32-1 could be detected when the input sound level variation dI is within a pre-specified sound level variation threshold. The presence of feedback can also be detected in a similar way. The parameter is system dependent, but a typical level variation threshold may have a value of 3 dB for detecting established feedback and the range for the level variation threshold for detecting the onset of feedback can be somewhat larger, e.g. 5 dB.

The input sound level modulation parameter fm represents the modulation of the input sound level due to the feedback path and the compression characteristics of the non-linear hearing aid. The presence of feedback in the bandpass input signal 32-1 can be detected when the input sound level modulation parameter fm has a value that is within a pre-specified modulation frequency range. For instance, the value of the input sound level modulation parameter fm may be in the range of a few Hz to a few hundred Hz during feedback. This parameter is also used to detect the onset of feedback. In a typical situation, the input sound level modulation parameter fm can be in the 3–5 Hz range for detecting the onset and presence of feedback. Again, this parameter is strongly influenced by the actual hearing aid system and other systems may require a much larger upper limit for this range.

The rise time duration parameter $t_r$ represents the amount of time required for the magnitude of the input sound level to cross over the feedback threshold level $I_0$. If the rise time duration $t_r$ indicates an input sound level that persistently increases for an amount of time greater than a pre-specified rise time duration threshold, then the onset of feedback can be detected in the bandpass input signal 32-1. Alternatively, the presence of feedback can be detected based on the time duration $t_d$ for which the input sound level is greater than the feedback level threshold $I_0$. The time duration $t_d$ can be compared to a pre-specified time duration threshold. This parameter is system dependent. A typical range of values for $t_r$ and $t_d$ is 20 to 50 ms and 40 to 100 ms respectively. Preferably, the values of $t_r$ and $t_d$ can be set to 40 ms and 50 ms respectively. However, this parameter is also strongly system dependent.

The gain differential parameter represents the difference in the calculated gain that is applied to the bandpass input signal 32-1 compared to the maximum gain that can be applied. The maximum gain for the hearing aid system may vary depending on frequency and is determined when the hearing aid system is fitted to the user. The presence of feedback can be detected in the bandpass input signal 32-1 when the calculated gain is close to the maximum gain, i.e. the gain differential is small and less than a pre-specified gain differential margin as will be described further below. Some exemplary gain differential margins may be 5, 10, 15 or 20 dB. Alternatively, the rate at which the gain differential decreases in magnitude can be used to indicate the onset of feedback, or the presence of feedback.

The feedback detector 42-1 may combine two or more of the above-noted parameters when determining whether a feedback condition is present within the input band signal 32-1 (i.e. feedback is present or the onset of feedback is eminent). The inventors have found that combining two or more of the parameters results in more reliable detection of potential feedback. While using fewer parameters to detect the onset or the presence of a feedback condition can lead to a successful result, the inventors have found that using all possible parameters together results in a more reliable and a rapid suppression or prevention of feedback. A typical combination the inventors used in the preferred implementation is $I_o$=48 dB, $I_d$=3 dB, dI=±3 dB, $t_r$=40 ms, $t_d$=50 ms, gain differential=12 dB, and fm=3.5 Hz. For example, monitoring a bandpass input signal during the time period $t_r$, leads to detection during the buildup phase, and a gain reduction, to address the buildup of feedback as described below, can already begin to be applied during the time period $t_d$. The inventors have observed cancellation of feedback in a time as short as 50 ms after onset. When feedback is already present, feedback detection and suppression can typically occur within 60 ms. The gain differential parameter is particularly important to the detection of feedback during the initial feedback buildup stage. The feedback signal is quickly distinguishable from normal speech or background noise, because the gain of the hearing aid system 10 usually reaches a maximum value during the feedback buildup phase. When the hearing aid system 10 is stabilized in a feedback condition the actual gain is effectively reduced by the compression in the system. Since the feedback pattern can be quickly recognized in a short time, during the feedback buildup phase or during the occurrence of feedback, each detection parameter contributes to the certainty of feedback detection.

Although FIG. 4 is directed towards the case of a non-linear hearing aid that uses a compression algorithm, some of the above-noted parameters can be used for detecting a feedback condition for a bandpass input signal in a linear hearing aid. These parameters include input sound level variation, rise time duration and input sound level. The linear hearing aid is a special case of the more general non-linear hearing aid system, and the typical values for the detection parameters stated above also apply to the linear hearing aid case.

When a feedback condition has been detected in one of the bandpass input signals 32-1, 32-2, . . . , 32-N, it is clear that the corresponding calculated gain value, which is calculated by the amplification unit, is higher than the stable gain for the hearing aid system 10 and the hearing aid system 10 is unstable. In accordance with the present invention, the corresponding adaptive feedback canceller 44-1, 44-2, . . . , 44-N applies a gain modification factor G-1, G-2, . . . , G-N for adjusting the gain applied to the bandpass input signal having the feedback condition. The magnitude of the gain modification factor and the amount of time for which the gain modification factor is applied are controlled so that the hearing aid system delivers the output sound signal 40 to the user of the hearing aid system 10 with natural sound quality, required signal strength, and without feedback.

Figure 5:
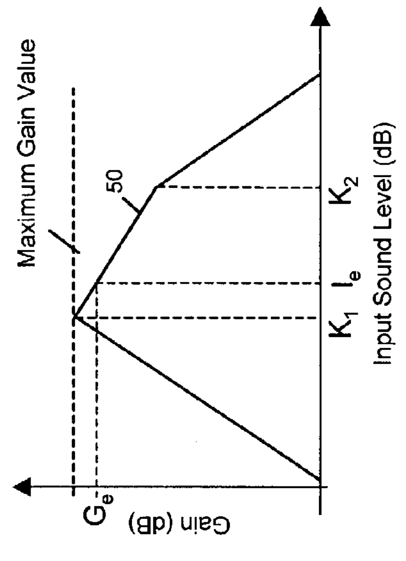
FIG. 5 is an exemplary plot of a gain curve for the hearing aid system of FIG. 1.

Referring now to FIG. 5, shown therein is an exemplary gain curve 50 that is applied to a bandpass input signal for a non-linear hearing aid which uses compression. The gain curve 50 provides the calculated gain value based on the input sound level. For example, for input sound level $I_e$, the calculated gain value is $G_e$. The gain curve 50 is piecewise linear with two knee-points $K_1$ and $K_2$. The gain curve 50 provides small gain values for low input sound levels (i.e. close to the origin of the gain curve 50) since these input sound levels are associated with microphone noise, environmental noise and system noise. The gain curve 50 then increases linearly to the first knee-point $K_1$ at which point the gain curve 50 has a maximum gain value. After the first knee-point $K_1$, compression begins to be applied. Accordingly, the magnitude of the calculated gain value corresponding to the input sound levels above the first knee-point $K_1$ begins to decrease. The location of the first knee-point $K_1$ depends on the hearing loss of the user of the hearing aid system 10 but may typically be 45 dB SPL, for example. After the second knee point $K_2$, the magnitude of the calculated gain value begins to decrease at a faster rate, since sounds associated with input sound levels above $K_2$ correspond to a very loud sound such as airplane noise.

The hearing aid system 10 may contain a different gain curve for each of the N frequency bands. For example, each gain curve may have a similar general shape but different values for the knee-points, or both the shapes and knee-points may differ from band to band. A gain curve for a linear hearing aid system is a special case of the gain curve for a non-linear hearing aid system. The gain curve for the linear hearing aid system usually exhibits a constant gain value up to the knee-point after which the gain curve decreases. The gain curves shown herein are exemplary and it is well known to those skilled in the art, that the slopes of these curves could be linear or curved and that the knee points can be abrupt or rounded.

Figure 6:
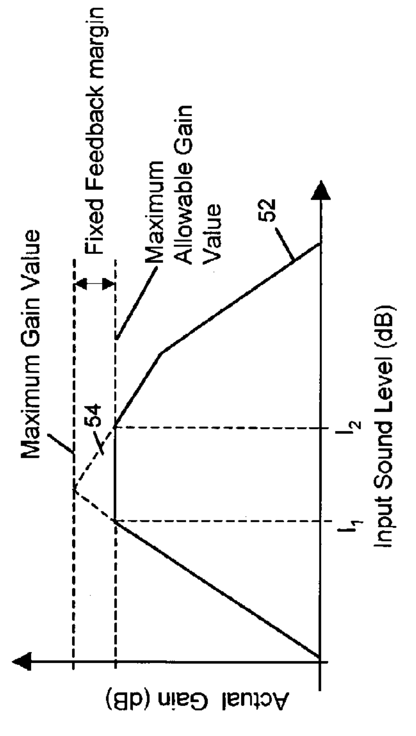
FIG. 6 is an exemplary plot of an actual gain curve for the hearing aid system of FIG. 1 when a fixed feedback margin is applied by the hearing aid system.

Referring now to FIG. 6, shown therein is an actual gain curve 52 that results due to the use of the adaptive feedback canceller 44-1. The adaptive feedback canceller 44-1 defines a feedback margin with respect to the maximum gain value of gain curve 50. The lower level of the feedback margin defines a maximum allowable gain value for the bandpass input signal 32-1, which results because of the presence of a feedback condition. In the case of FIG. 6, the feedback margin is a fixed feedback margin, however, the adaptive feedback canceller 44-1 may also apply an adaptive feedback margin as discussed below. Exemplary values for the magnitude of the fixed feedback margin are 6, 10, 12 or 18 dB. Through experiments the inventors have found that a fixed feedback margin of 12 dB is preferable for adaptively canceling feedback while minimally disrupting the sound quality of the output sound signal 40.

The adaptive feedback canceller 44-1 calculates a gain modification factor G-1 such that the actual gain value that is applied to the bandpass input signal 32-1 is less than or equal to the maximum allowable gain value when a feedback condition is detected within the bandpass input signal 32-1. The adaptive feedback canceller 44-1 preferably calculates the magnitude of the gain modification factor such that the actual gain value is limited to the maximum allowable gain value. Advantageously, the adaptive feedback canceller 44-1 calculates gain modification factors for a narrow range of input sound level values (i.e. from input sound level $I_1$ to input sound level $I_2$ in the example of FIG. 6). This provides minimal disruption to the sound quality of the overall dynamic sound signal that is experienced by the user of the hearing aid system 10. In addition, the adaptive feedback canceller 44-1 preferably adaptively calculates the gain modification factor based on the amount that the calculated gain value is over the maximum allowable gain value. For example, assuming a maximum allowable gain value of 40 dB, the adaptive gain factor for a first calculated gain value of 43 dB is preferably −3 dB and the adaptive gain factor for a second calculated gain value of 48 dB is preferably −8 dB. The maximum gain reduction provided by the gain modification factor occurs when the input sound level coincides with the first knee-point $K_1$. Accordingly, the adaptive feedback canceller 44-1 is not overly aggressive when calculating the gain modification factor for all input sound levels for which a feedback condition exists.

It should be understood that the gain adjustment provided by the gain modification factor is temporal and will be adaptively applied and adaptively removed in accordance with the continuous feedback detection provided by the feedback detector 42-1. This will allow the overall output sound signal, which may contain speech and/or music, to be essentially unaffected since the actual gain has been temporarily modified in time and frequency in order to remove feedback in one or more of the bandpass input signals 32-1, 32-2, . . . , 32-N for which a feedback condition has been detected.

The adaptive feedback canceller 44-1 works well in most situations when the fixed feedback margin is applied. However, because a fixed feedback margin is used, the adaptive gain modification factor may not necessarily be optimized to provide the best performance for a wide variety of different types of hearing aid systems and for different degrees of feedback. For instance, if a large fixed feedback margin is used, the adaptive feedback canceller 44-1 might over-react to feedback and reduce the gain more than is required. This may cause unnecessary and undesirable sound quality degradation in the output sound signal 40. In the other extreme, if a small fixed feedback margin is applied, the adaptive feedback canceller 44-1 might under-react to the feedback and not cancel the feedback completely.

The above-noted considerations led to the use of an adaptive feedback margin in which the adaptive feedback canceller 44-1 adaptively adjusts the magnitude of the feedback margin in order to optimize feedback cancellation and the sound quality of the output sound signal 40. Once the feedback detector 42-1 detects a feedback condition, the adaptive feedback canceller 44-1 applies a feedback margin having a first magnitude that is a low value such as 3 dB, for example. If the feedback is cancelled immediately, as indicated by the feedback detection signal FD-1 provided by the feedback detector 42-1, the adaptive feedback canceller 44-1 will continue to apply the low magnitude feedback margin. However, if feedback still exists or continues to buildup, the adaptive feedback canceller 44-1 adaptively increases the magnitude of the adaptive feedback margin. In this fashion, the magnitude of the adaptive feedback margin is progressively increased until the feedback is cancelled or the feedback buildup is stopped.

The step-size that is used in increasing the adaptive feedback margin may comprise large steps for aggressively attacking the feedback condition. Alternatively, the step-size may comprise small steps to optimize the balance between canceling the feedback condition and maintaining good sound quality in the output sound signal 40 at all times. In addition, the speed with which, or the time duration that expires before, the magnitude of the adaptive feedback margin is increased can be varied to aggressively attack the feedback condition. For example, the adaptive feedback canceller 44-1 may wait 5 ms before increasing the magnitude of the adaptive feedback margin. The time duration can also depend on the reaction time (i.e. attack and release times) of the hearing aid system. The time duration should be short (i.e. fast) for a hearing aid system with fast attack and release times.

Figure 7:
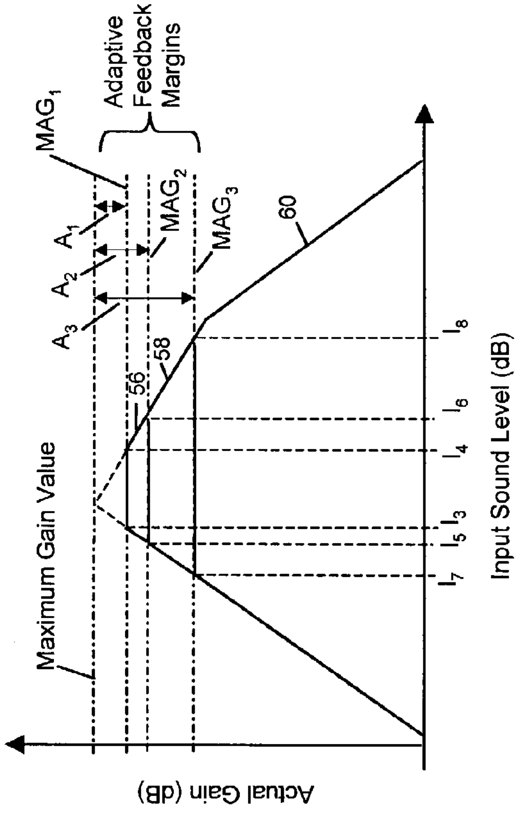
FIG. 7 is an exemplary plot of an actual gain curve for the hearing aid system of FIG. 1 when an adaptive feedback margin is applied by the hearing aid system.

Referring now to FIG. 7, shown therein are actual gain curves that result when the adaptive feedback canceller 44 employs an adaptive feedback margin. In this example, the adaptive feedback canceller 44 defines an adaptive feedback margin having three possible magnitudes $A_1$, $A_2$ and $A_3$ with respect to the maximum gain value of gain curve 50. Accordingly, the three magnitudes $A_1$, $A_2$ and $A_3$ of the adaptive feedback margins result in three maximum allowable gain values $MAG_1$, $MAG_2$ and $MAG_3$ and three corresponding actual gain curves 56, 58 and 60.

The operation of the adaptive feedback canceller 44 with respect to a given adaptive feedback margin is similar to the operation previously described for the case of the fixed feedback margin and accordingly will not be discussed further. However, it is interesting to note that for each adaptive feedback margin, the adaptive gain modification factors are calculated for a different input sound level range and the range of the values of the adaptive gain modification factors (which relates to the magnitudes of the adaptive feedback margins $A_1$, $A_2$ and $A_3$) also increases. For example, with an adaptive feedback margin having magnitude $A_1$, the input sound levels in the range of $I_3$ to $I_4$ are modified by the adaptive gain modification factor. With an adaptive feedback margin having magnitude $A_2$, the input sound levels in the range of $I_5$ to $I_6$ are modified by the adaptive gain modification factor. Finally, with an adaptive feedback margin having magnitude $A_3$, the input sound levels in the range of $I_7$ to $I_8$ are modified by the adaptive gain modification factor. Accordingly, an adaptive feedback margin with the largest magnitude $A_3$ affects the largest range of input sound levels by possibly the largest amount.

The hearing aid system 10 may employ a variety of combinations for the feedback margins. For instance, the hearing aid system 10 may employ only fixed feedback margins or only adaptive feedback margins. Alternatively, the hearing aid system 10 may employ a combination of both fixed and adaptive feedback margins at the same time. For example, the sub-units of the adaptive feedback cancellation unit 18 that process bandpass input signals which correspond to a low frequency portion of the input frequency spectrum may employ fixed feedback margins while the sub-units of the adaptive feedback cancellation unit 18 that process bandpass input signals which correspond to a high frequency portion of the input frequency spectrum, which are susceptible to feedback path variations, may employ adaptive feedback margins.

As is well known to those skilled in the art, it is common for hearing aid systems to provide a volume control function for the user of the hearing aid system. The volume control allows the user to adjust the sound level of the time domain output signal 36 (which affects the output sound signal 40 in a likewise fashion) by turning a potentiometer wheel or depressing a push button switch. The amount of adjustment provided by the volume control may range, for example, from 0 to 10 dB or 0 to 30 dB with step-size adjustments that can be as fine as 0.1 dB. Accordingly, the user has the ability to adjust the actual gain of the hearing aid system through volume control which effects the function of the adaptive feedback cancellers 44-1. Accordingly, the volume control must be taken into account by the adaptive feedback canceller 44-1. The volume control may be positioned before or after the feedback cancellation unit 18. In practice, the volume control may be applied prior to the analysis unit 16 or after the synthesis unit 20. Alternatively, the volume control may be placed between the analysis unit 16 and the adaptive feedback cancellation unit 18 or between the adaptive feedback cancellation unit 18 and the synthesis unit 20.

Figure 8:
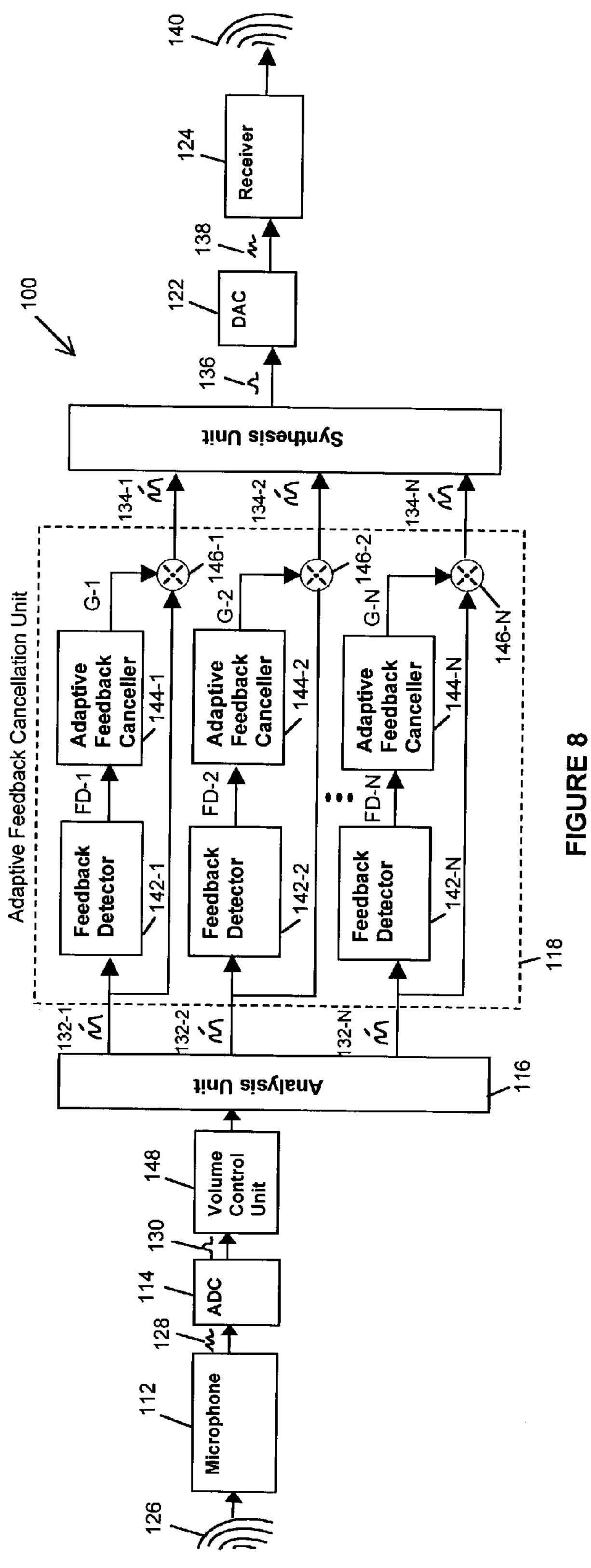
FIG. 8 is a block diagram of an alternative embodiment of a hearing aid system for adaptively reducing feedback while incorporating a volume control unit before an adaptive feedback cancellation unit in accordance with the present invention.

Referring now to FIG. 8, shown therein is an alternative embodiment of the hearing aid system 100 that incorporates a volume control unit 148. The majority of the components of the hearing aid system 100 function in the same way as for hearing aid system 10 and have been numbered in a likewise fashion but offset by a factor of 100. The volume control unit 148 of the hearing aid system 100 is located upstream from the analysis unit 116.

Figure 9:
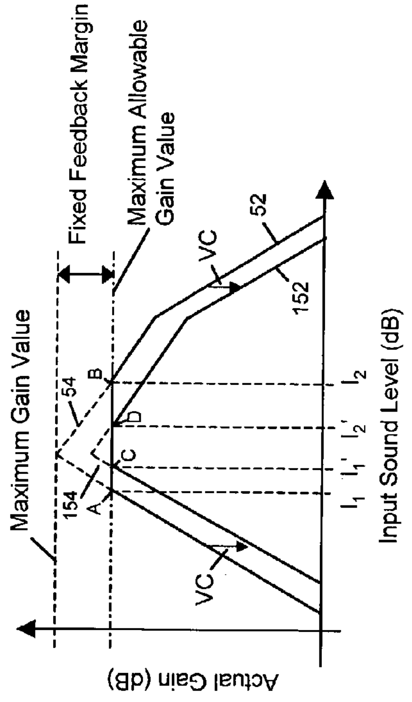
FIG. 9 is an exemplary plot of an actual gain curve for the hearing aid system of FIG. 8 when a fixed feedback margin is applied by the hearing aid system.

Referring now to FIG. 9, shown therein are two actual gain curves 52 and 152 for the case in which the adaptive feedback canceller 144-1 is utilizing a fixed feedback margin. The first actual gain curve 52 corresponds to the situation in which the volume control unit 148 is at a maximum setting, i.e., the user of the hearing aid system 100 has not used the volume control unit 148 to decrease the sound level of the output sound signal 140. In this case, the adaptive feedback canceller 144-1 calculates the adaptive gain modification factor for input sound levels in the range of l1 to l2 which corresponds to line segment AB on the actual gain curve 52.

The second actual gain curve 152 corresponds to the situation in which the user of the hearing aid system 100 has used the volume control unit 148 to decrease the sound level of the output signal 140 by an amount VC dB. In this case, the actual gain curve 152 is shifted downwards by the amount VC dB. The magnitude of the fixed feedback margin and the maximum allowable gain value are not affected by the reduction in actual gain produced by the volume control unit 148. However, the adaptive feedback canceller 144-1 calculates the adaptive gain modification factor for input sound levels in the range of $I_1'$ to $I_2'$ which corresponds to line segment CD on the actual gain curve 152. The input sound level range of $I_1'$ to $I_2'$ is smaller than the input sound level range of $I_1$ to $I_2$. This is also seen by the smaller size of dotted portion 154 compared to the dotted portion 54 which indicates that the range of values for the magnitude of the adaptive gain modification factor is smaller with a reduced volume control setting.

Figure 10:
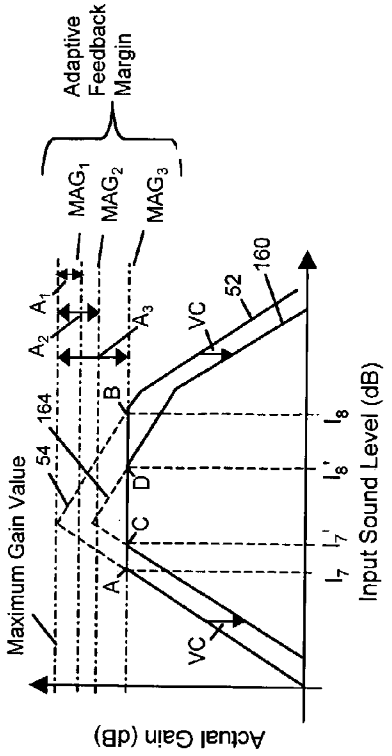
FIG. 10 is an exemplary plot of an actual gain curve for the hearing aid system of FIG. 8 when an adaptive feedback margin is applied by the hearing aid system.

Referring now to FIG. 10, shown therein are two actual gain curves 52 and 160 for the case in which the adaptive feedback canceller 144-1 is utilizing an adaptive feedback margin (only one magnitude of the adaptive feedback margin will be discussed for simplicity). The first actual gain curve 52 corresponds to the situation in which the volume control unit 148 is at a maximum setting and the adaptive feedback margin has a magnitude of $A_3$ with a corresponding maximum allowable gain value of $MAG_3$. In this case, the adaptive feedback canceller 144-1 calculates the adaptive gain modification factor for input sound levels in the range of $I_7$ to $I_8$ which corresponds to line segment AB on the actual gain curve 52.

The second actual gain curve 160 corresponds to the situation in which the user of the hearing aid system 100 has used the volume control unit 148 to decrease the sound level of the output signal 140 by an amount VC dB thereby shifting the curve 160 downwards by the amount VC dB. The magnitude of the adaptive feedback margin $A_3$ and the maximum allowable gain value $MAG_3$ are not affected by the reduction in actual gain produced by the volume control unit 148. However, the adaptive feedback canceller 144 calculates the adaptive gain modification factor for input sound levels in the range of $I_7'$ to $I_8'$ which corresponds to line segment CD on the actual gain curve 160. The input sound level range of $I_7'$ to $I_8'$ is smaller than the input sound level range of $I_7$ to $I_8$. This is also seen by the smaller size of dotted portion 164 compared to the dotted portion 54 which indicates that the range of possible values for the magnitude of the adaptive gain modification factor is smaller with a reduced volume control setting.

Figure 11:
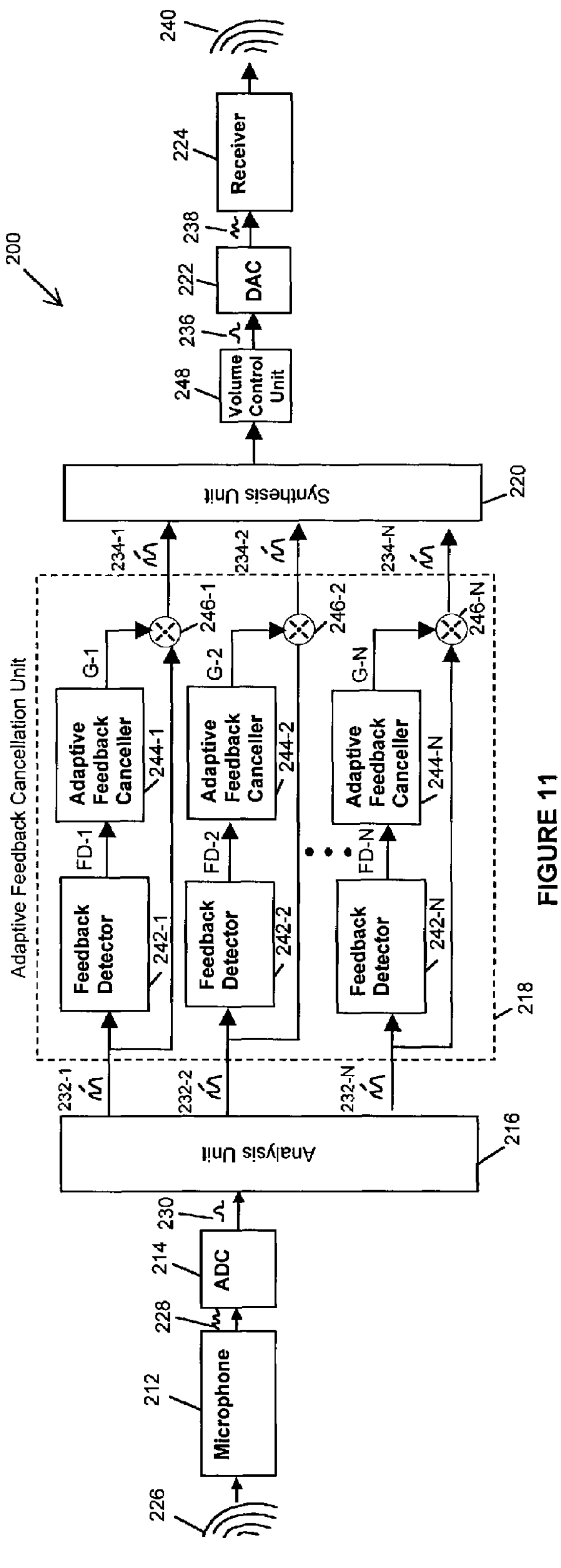
FIG. 11 is a block diagram of another alternative embodiment of a hearing aid system for adaptively reducing feedback while incorporating a volume control unit after an adaptive feedback cancellation unit in accordance with the present invention.

Referring now to FIG. 11, shown therein is another alternative embodiment of the hearing aid system 200 that incorporates a volume control unit 248. The majority of the components of the hearing aid system 200 function in the same way as for hearing aid system 10 and have been numbered in a likewise fashion but offset by a factor of 200. The volume control unit 248 of the hearing aid system 200 is located downstream from the synthesis unit 216.

Figure 12:
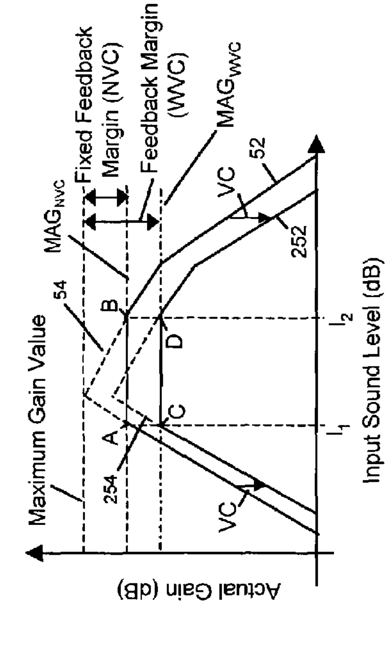
FIG. 12 is an exemplary plot of an actual gain curve for the hearing aid system of FIG. 11 when a fixed feedback margin is applied by the hearing aid system; and, FIG. 13 is an exemplary plot of an actual gain curve for the hearing aid system of FIG. 11 when an adaptive feedback margin is applied by the hearing aid system.

Referring now to FIG. 12, shown therein are two actual gain curves 52 and 252 for the case in which the adaptive feedback canceller 244 is utilizing a fixed feedback margin. The first actual gain curve 52 corresponds to the situation in which the volume control unit 248 is at a maximum setting. In this case, the adaptive feedback canceller 244 applies a fixed feedback margin (NVC) with an associated maximum allowable gain value $MAG_{NVC}$ (NVC means that the volume control setting is at a maximum and that there has not been a reduction in the volume control setting). The adaptive feedback canceller 244 calculates the adaptive gain modification factor for input sound levels in the range of $I_1$ to $I_2$ which corresponds to line segment AB on the actual gain curve 52.

The second actual gain curve 252 corresponds to the situation in which the user of the hearing aid system 200 has used the volume control unit 248 to decrease the sound level of the output signal 240 by an amount VC dB. In this case, the actual gain curve 252 is shifted downwards by the amount VC dB with respect to actual gain curve 52. The magnitude of the fixed feedback margin and the maximum allowable gain value are affected by the adjustment in actual gain produced by the volume control unit 248 and are shifted downwards by the same amount of VC dB. The adaptive feedback canceller 244-1 is effectively applying a fixed feedback margin (WVC) with an associated maximum allowable gain value $MAG_{wvc}$ with respect to the maximum gain of the hearing aid system 200 (WVC means that the volume control setting is at a reduced setting). Accordingly, the adaptive feedback canceller 244 calculates the adaptive gain modification factor for input sound levels in the same range of $I_1$ to $I_2$ corresponding to line segment CD, which has the same length as line segment AB, on the actual gain curve 252. Further, dotted portion 254 is the same as the dotted portion 54 which indicates that the range of values for the magnitude of the adaptive gain modification factor remains the same with a reduced volume control setting in this case.

Figure 13:
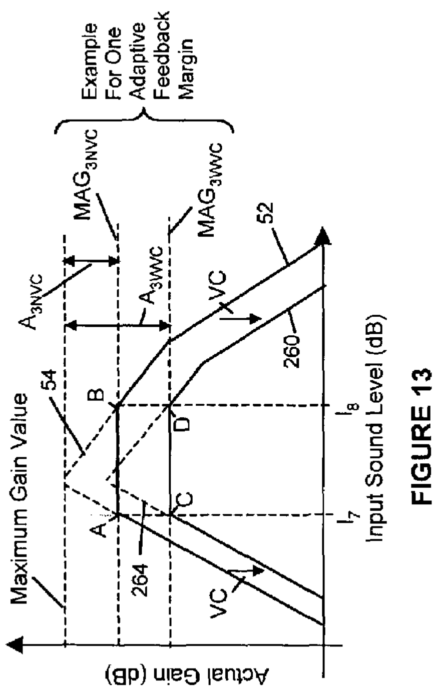

Referring now to FIG. 13, shown therein are two actual gain curves 52 and 260 for the case in which the adaptive feedback canceller 244-1 utilizes an adaptive feedback margin (only one magnitude of the adaptive feedback margin is shown in FIG. 13 and discussed for simplicity). The first actual gain curve 52 corresponds to the situation in which the volume control unit 248 is at a maximum setting and the adaptive feedback margin has a magnitude of $A_{3NVC}$ with a corresponding maximum allowable gain value of $MAG_{3NVC}$. In this case, the adaptive feedback canceller 244-1 calculates the adaptive gain modification factor for input sound levels in the range of $I_7$ to $I_8$ which corresponds to line segment AB on the actual gain curve 52.

The second actual gain curve 260 corresponds to the situation in which the user of the hearing aid system 200 has used the volume control unit 248 to decrease the sound level of the output signal 240 by an amount VC dB thereby shifting the curve 260 downwards by the amount VC dB with respect to actual gain curve 52. However, in this case, there is a corresponding increase in the magnitude of the adaptive feedback margin $A_{3WVC}$ and a downward shift in the maximum allowable gain value $MAG_{3WVC}$ by the amount VC dB. Accordingly, the adaptive feedback canceller 244-1 calculates the adaptive gain modification factor for input sound levels in the range of $I_7$ to $I_8$ corresponding to line segment CD, which has the same length as line segment AB, on the actual gain curve 260. Further, the dotted portion 264 has the same size compared to the dotted portion 54 which indicates that the range of values for the magnitude of the adaptive gain modification factor remains the same with a reduced volume control setting in this case.

The inventors have found that, with the hearing aid system of the present invention, detection and cancellation of the feedback condition takes place in less than 100 ms which is before feedback is fully built up and becomes noticeable to the hearing aid user. In contrast, most prior art feedback cancellation technologies usually require in excess of 400 ms for feedback detection and cancellation during which the feedback has already built up to a steady state level which can be extremely uncomfortable to the hearing aid user. The inventors have also found that the inventive hearing aid system is capable of detecting and canceling multiple feedback paths occurring in several of the N frequency regions. For example, the inventors have observed as many as seven feedback frequencies at one time.

It should be understood that various modifications can be made to the preferred embodiments described and illustrated herein, without departing from the present invention, the scope of which is defined in the appended claims. For instance, it should be understood that the adaptive feedback cancellation scheme of the present invention may be employed for any type of audio system and need not be restricted to hearing aid systems. The application of this adaptive feedback cancellation scheme may involve having alternative shapes for the gain curves but the underlying principles of the invention would still apply.

In addition, it should be understood that there can be an alternative embodiment in which not every sub-unit of the adaptive cancellation unit addresses feedback since feedback does not usually occur for some frequencies (i.e. less than 1000 Hz). Accordingly, in this alternative embodiment, at least one or some of the sub-units address feedback and contain the feedback detector, the adaptive feedback canceller and the multiplier.

It should also be understood by those skilled in the art that the units of the hearing aid system are typically implemented in a digital signal processor. Accordingly, the functionality of the feedback detector, the adaptive feedback canceller and the multiplier of one of the sub-units of the adaptive feedback cancellation unit may be implemented within the same means.

The invention claimed is:

1. An audio system for receiving a time domain input signal having an input frequency spectrum and for providing a time domain output signal, said audio system being adapted to remove a feedback condition within said time domain input signal, said system comprising:

a) an analysis unit for receiving said time domain input signal and providing N bandpass input signals, each of said bandpass input signals corresponding to a portion of said input frequency spectrum, and wherein N is a positive integer;

b) an adaptive feedback cancellation unit coupled to said analysis unit for receiving said N bandpass input signals and providing N bandpass output signals, said adaptive feedback cancellation unit comprising N sub-units, wherein at least one sub-unit is adapted to cancel feedback, the at least one sub-unit including:

(i) a feedback detector coupled to said analysis unit for receiving one of said bandpass input signals and providing a feedback detection signal for indicating the presence of said feedback condition in said one of said bandpass input signals;

(ii) an adaptive feedback canceller coupled to said feedback detector for receiving said feedback detection signal and providing an adaptive gain modification factor for adjusting gain when said feedback detection signal indicates the presence of said feedback condition within said one of said bandpass input signals; and, (iii) a multiplier coupled to said adaptive feedback canceller and said analysis unit for providing one of said bandpass output signals based on said one of said bandpass input signals and the adaptive gain modification factor; and, c) a synthesis unit for receiving said N bandpass output signals and for providing said time domain output signal.

2. The audio system of claim 1, wherein each of the sub-units is adapted to cancel feedback and each of the sub-units include the feedback detector, the adaptive feedback canceller and the multiplier.

3. The audio system of claim 1, wherein said feedback detector of the at least one sub-unit is adapted to detect said feedback condition during feedback buildup, thereby allowing for removal of said feedback condition prior to audible feedback occurring in said output signal.

4. The audio system of claim 1, wherein said feedback detector of the at least one sub-unit detects said feedback condition based on input sound level variation of said one of said bandpass input signals.

5. The audio system of claim 1, wherein said feedback detector of the at least one sub-unit detects said feedback condition based on input sound level modulation of said one of said bandpass input signals.

6. The audio system of claim 1, wherein said feedback detector of the at least one sub-unit detects said feedback condition based on rise time duration of said one of said bandpass input signals.

7. The audio system of claim 1, wherein said feedback detector of the at least one sub-unit detects said feedback condition based on input sound level of said one of said bandpass input signals.

8. The audio system of claim 1, wherein said feedback detector of the at least one sub-unit detects said feedback condition based on gain differential of said one of said bandpass input signals.

9. The audio system of claim 1, wherein said feedback detector of the at least one sub-unit detects said feedback condition based on a combination of two or more properties of said one of said bandpass input signals, said properties comprising: input sound level variation, input sound level modulation, rise time duration, input sound level and gain differential.

10. The audio system of claim 1, wherein said adaptive feedback canceller of the at least one sub-unit calculates said adaptive gain modification factor for a range of sound levels of said one of said bandpass input signals.

11. The audio system of claim 1, wherein for said one of said N bandpass input signals, said audio system comprises a gain curve for modifying a sound level of said one of said N bandpass input signals by a calculated gain value, said calculated gain value being obtained from said gain curve based on said sound level, said gain curve having a maximum gain value.

12. The audio system of claim 11, wherein said adaptive feedback canceller of the at least one sub-unit defines a feedback margin with respect to said maximum gain value for providing a maximum allowable gain value when said feedback condition exists, wherein during said feedback condition, said calculated gain value is larger than said maximum allowable gain value and said adaptive feedback canceller of the at least one sub-unit calculates said adaptive gain modification factor for providing said one of said bandpass output signals with an actual gain value, said actual gain value being less than or equal to said maximum allowable gain value.

13. The audio system of claim 12, wherein said feedback margin is a fixed feedback margin.

14. The audio system of claim 12, wherein said feedback margin is an adaptive feedback margin having a magnitude, wherein said adaptive feedback canceller of the at least one sub-unit progressively increases said magnitude of said adaptive feedback margin until said feedback condition ceases to exist in said one of said bandpass input signals.

15. The audio system of claim 12, wherein said adaptive feedback canceller of the at least one sub-unit employs a fixed feedback margin when said one of said bandpass input signals corresponds to a low frequency portion of said input frequency spectrum, and said adaptive feedback canceller of the at least one sub-unit further employs an adaptive feedback margin when said one of said bandpass input signals corresponds to a high frequency portion of said input frequency spectrum.

16. The audio system of claim 12, wherein said audio system further comprises a volume control unit located upstream from said adaptive feedback cancellation unit for allowing a user of said audio system to produce a sound level adjustment in said output signal, wherein during said sound level adjustment, said adaptive gain modification factor is calculated for a smaller range of said input sound level of said one of said bandpass input signals.

17. The audio system of claim 12, wherein said audio system further comprises a volume control unit located downstream from said adaptive feedback cancellation unit for allowing a user of said audio system to produce a sound level adjustment in said output signal, wherein during said sound level adjustment, said maximum allowable gain value is similarly adjusted and said adaptive gain modification factor is calculated for a similar range of said input sound level of said one of said bandpass input signals.

18. A method for removing a feedback condition in an audio system, said audio system being adapted to receive a time domain input signal having an input frequency spectrum and provide a time domain output signal, said method comprising:

a) converting said time domain input signal into one or more bandpass input signals, each of said one or more bandpass input signals corresponding to a portion of said input frequency spectrum;

b) providing one or more bandpass output signals corresponding to said one or more bandpass input signals wherein for at least one of said one or more bandpass input signals, the method comprises:

(i) providing a feedback detection signal for indicating the presence of said feedback condition in said at least one of said one or more bandpass input signals;

(ii) providing an adaptive gain modification factor for adjusting gain when said feedback detection signal indicates the presence of said feedback condition within said at least one of said one or more bandpass input signals; and, (iii) providing one of said one or more bandpass output signals by multiplying said at least one of said one or more bandpass input signals and the adaptive gain modification factor; and, c) combining said one or more bandpass output signals for providing said time domain output signal.

19. The method of claim 18, wherein steps b(i) to b(iii) of the method are applied to each of said one or more bandpass input signals.

20. The method of claim 18, wherein step (b)(i) comprises detecting said feedback condition during feedback buildup, thereby allowing for removal of said feedback condition prior to audible feedback occurring in said output signal.

21. The method of claim 18, wherein step (b)(i) comprises examining input sound level variation of said at least one of said one or more bandpass input signals.

22. The method of claim 18, wherein step (b)(i) comprises examining input sound level modulation of said at least one of said one or more bandpass input signals.

23. The method of claim 18, wherein step (b)(i) comprises examining rise time duration of said at least one of said one or more bandpass input signals.

24. The method of claim 18, wherein step (b)(i) comprises examining input sound level of said at least one of said one or more bandpass input signals.

25. The method of claim 18, wherein step (b)(i) comprises examining gain differential of said at least one of said one or more band pass input signals.

26. The method of claim 18, wherein step (b)(i) comprises examining two or more properties of said at least one of said one or more bandpass input signals, said properties comprising: input sound level variation, input sound level modulation, rise time duration, input sound level and gain differential.

27. The method of claim 18, wherein step (b)(ii) further comprises calculating said adaptive gain modification factor for a range of input levels of said at least one of said one or more bandpass input signals.

28. The method of claim 18, wherein prior to step (b), said method further comprises modifying a sound level of said one or more bandpass input signals by applying a calculated gain value, said calculated gain value being obtained from a gain curve based on said sound level, said gain curve having a maximum gain value.

29. The method of claim 28, wherein providing said adaptive gain modification factor comprises defining a feedback margin with respect to said maximum gain value for providing a maximum allowable gain value when said feedback condition exists, wherein during said feedback condition, said calculated gain value is larger than said maximum allowable gain value and said method comprises calculating said adaptive gain modification factor for providing said one or more bandpass output signals with an actual gain value, said actual gain value being less than or equal to said maximum allowable gain value.

30. The method of claim 29, wherein step (b)(ii) comprises defining a fixed feedback margin for said feedback margin.

31. The method of claim 29, wherein step (b)(ii) comprises defining an adaptive feedback margin for said feedback margin, said adaptive feedback margin having a magnitude, wherein step (b)(ii) further comprises progressively increasing said magnitude of said adaptive feedback margin until said feedback condition ceases to exist in said at least one of said one or more bandpass input signals.

32. The method of claim 29, wherein step (b)(ii) comprises defining a fixed feedback margin when said at least one of said one or more bandpass input signals corresponds to a low frequency portion of said input frequency spectrum, and step (b)(ii) further comprises defining an adaptive feedback margin when said at least one of said one or more band pass input signals corresponds to a high frequency portion of said input frequency spectrum.

33. The method of claim 29, wherein said method further comprises allowing a user of said audio system to produce a sound level adjustment in said output signal prior to step (b), wherein during said sound level adjustment, said adaptive gain modification factor is calculated for a smaller range of said sound level of said one or more bandpass input signals.

34. The method of claim 29, wherein said method further comprises allowing a user of said audio system to produce a sound level adjustment in said output signal after step (b), wherein during said sound level adjustment, said maximum allowable gain value is effectively similarly adjusted and said adaptive gain modification factor is calculated for a similar range of said sound level of said one or more bandpass input signals.

* * * * *